United States Patent

Kirwan, Jr.

[11] Patent Number: 5,989,249
[45] Date of Patent: Nov. 23, 1999

[54] BIPOLAR SUCTION COAGULATOR

[75] Inventor: Lawrence T. Kirwan, Jr., Kingston, Mass.

[73] Assignee: Kirwan Surgical Products, Inc., Rockland, Mass.

[21] Appl. No.: 08/639,623

[22] Filed: Apr. 29, 1996

[51] Int. Cl.$^6$ .................................................. A61B 17/39
[52] U.S. Cl. ................................ 606/50; 606/40; 606/41
[58] Field of Search ........................... 606/37–42, 45–50; 604/21, 22, 35

[56] References Cited

U.S. PATENT DOCUMENTS

| | | | |
|---|---|---|---|
| Re. 33,925 | 5/1992 | Bales et al. | 606/48 |
| 3,828,780 | 8/1974 | Morrison, Jr. | |
| 3,974,833 | 8/1976 | Durden, III | 604/21 |
| 4,269,174 | 5/1981 | Adair | 606/50 |
| 4,381,007 | 4/1983 | Doss | 606/50 |
| 4,674,499 | 6/1987 | Pao | 606/50 |
| 4,932,952 | 6/1990 | Wojciechowicz, Jr. | 606/49 |
| 5,084,045 | 1/1992 | Helenowski | 606/48 |
| 5,277,696 | 1/1994 | Hagen | 606/49 |
| 5,312,401 | 5/1994 | Newton et al. | 606/46 |
| 5,403,311 | 4/1995 | Abele et al. | 606/49 |
| 5,409,487 | 4/1995 | Jalbert et al. | 606/48 |
| 5,520,685 | 5/1996 | Wojciechowicz | 606/49 |
| 5,827,275 | 10/1998 | Morris | 606/41 |

*Primary Examiner*—Michael Peffley
*Attorney, Agent, or Firm*—Weingarten, Schurgin, Gagnebin & Hayes LLP

[57] ABSTRACT

Disclosed is an electro surgical device for use by a surgeon to perform coagulation procedures to damaged tissue and evacuation procedures to related fluids. In one embodiment, the device comprises a first electrode having a first open end, a second open end, an outside surface, and a channel extending from the first open end to the second open end. The device further comprises a second electrode having a first end, a second end, an inside surface, and an outside surface. The inside surface of the second electrode is encased about the outside surface of the first electrode and electrically isolated by an insulator. The device further comprises first and second terminal pins each having a first end connected to the first and second electrodes, respectively, and a second end adapted to engage with the electrical generator. The device further comprises a housing having a suction port and a terminal pin portion. The suction port comprises an inner portion in communication with the second end of the first electrode and an outside portion adapted to engage with the suction device. Upon activation of the suction device, the surgeon may cause fluid to evacuate into the first end of the first electrode, flow through the channel, and exit the suction port to the suction device. Upon activation of the electrical generator, the surgeon may cause an electrical potential to be generated at and between the first end of the first electrode and the first end of the second electrode.

10 Claims, 1 Drawing Sheet

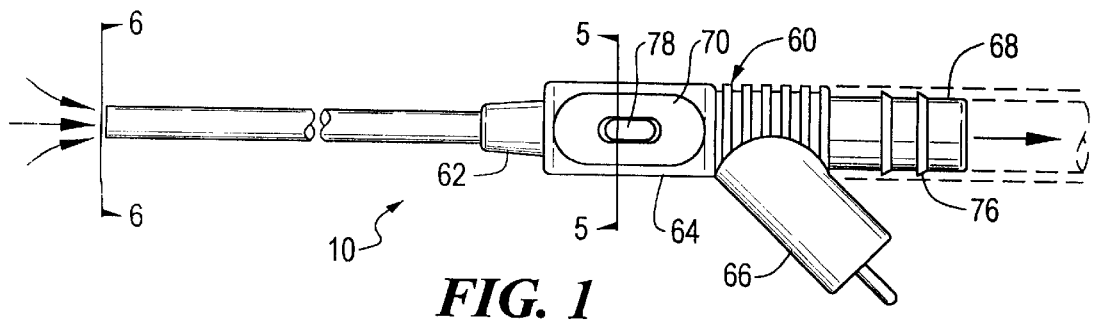
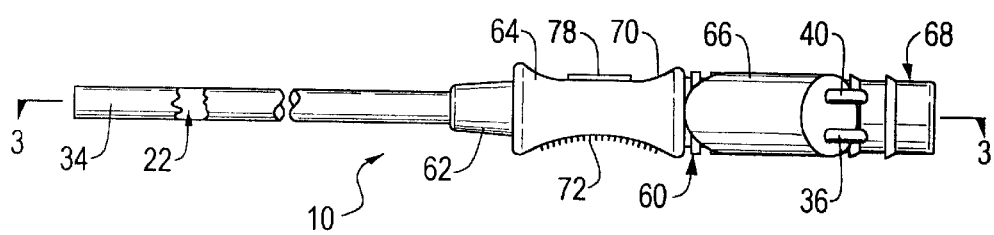
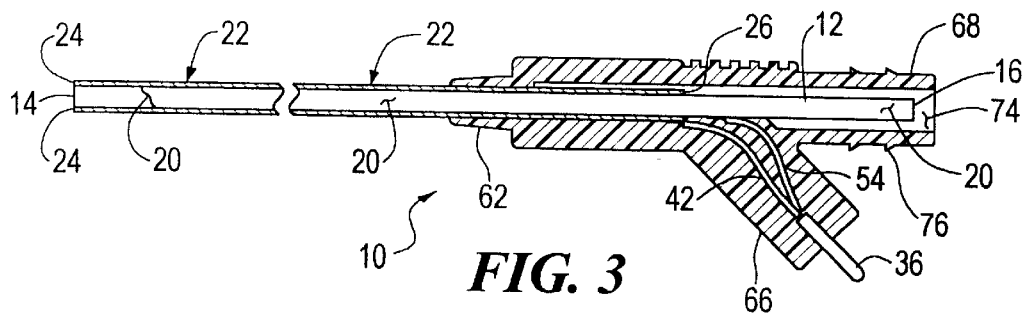
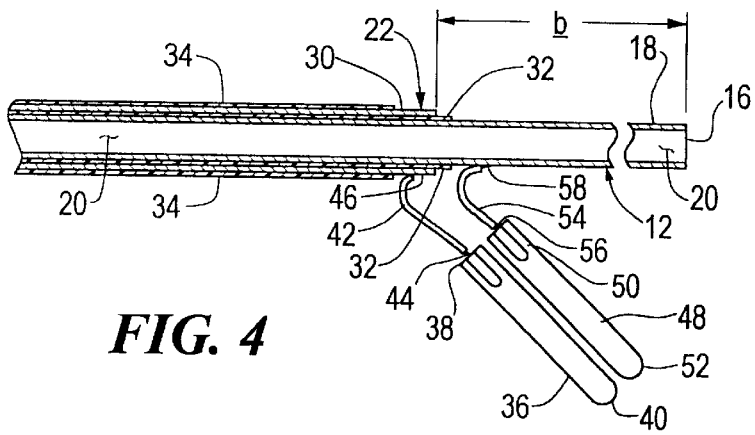
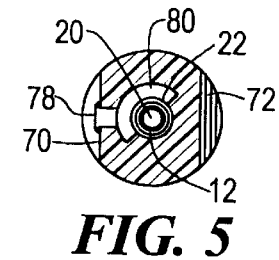
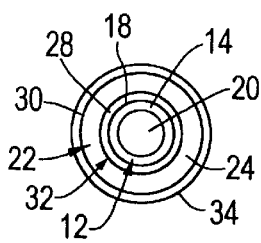

BIPOLAR SUCTION COAGULATOR

FIELD OF THE INVENTION

The present invention relates generally to medical devices. More specifically, the present invention relates to devices used to perform surgical procedures.

BACKGROUND OF THE INVENTION

Surgical devices are continuously being developed to allow surgeons to perform safer surgical procedures. U.S. Pat. No. 5,133,714 which is commonly assigned with the present application discloses a monopolar suction coagulator. With the device of U.S. Pat. No. 5,133,714, a surgeon can coagulate damaged tissue and evacuate related fluids as needed. Devices of the type exemplified by U.S. Pat. No. 5,133,714 have several drawbacks. Most principally, such devices are monopolar wherein one of the electrodes is formed as part of the device and the return electrode is attached to the patient in the form of a ground pad. Such devices require a high energy output in order to perform the coagulation process and it is very difficult for the surgeon to precisely apply the electrical energy output to only the damaged tissue and as a result surrounding tissue is often damaged. As such, for surgical procedures requiring very high precision and where it is imperative that surrounding tissue not be damaged (such as neurosurgery, endoscopic surgery, and sinusoidal surgery) such monopolar devices cannot be easily and effectively used.

SUMMARY OF THE PRESENT INVENTION

One object of the present invention is to provide a bipolar device that can be used by surgeons to perform coagulation of damaged tissue in a precise manner without damage to surrounding tissue and where evacuation of related fluids can be easily performed.

The present invention is an electro-surgical device for coagulation of damaged tissue and/or to evacuate related fluids. In one embodiment, the device comprises an inner electrode having a first end, a second end, and a channel to allow fluid to pass therethrough. The device further comprises an outer electrode having a first end, a second end, and an inner surface. The inner surface of the outer electrode is disposed in coaxial relationship about the outer surface of the inner electrode and electrically isolated by an insulator. The device further comprises first and second terminal pins each having one end connected by a jumper wire to the inner and outer electrodes, respectively. The other end of the terminal pins are adapted to engage with a bipolar electrosurgical generator. The device further comprises a housing into which the sub-assembly of the inner and outer electrodes, terminal pins, and jumper wires are molded. The housing comprises a suction port which is in communication with the channel of the inner electrode and can be engaged with a suction device or pump to evacuate fluid. The housing also comprises a suction control vent which is in communication with the suction port to selectively control the flow of fluid through the channel from a slow to a rapid flow rate.

Upon activation of the suction device and application of the suction control vent, a surgeon may cause fluid to enter the first end of the inner electrode, flow through the channel, and out the suction port to the suction device. Upon activation of the bipolar electrosurgical generator, a surgeon may cause a localized electrical potential to be generated at and between the first end of the inner electrode and the first end of the outer electrode. With the device of the present invention, a surgeon can perform coagulation of damaged tissue in a precise manner without damage to surrounding tissue and evacuate related fluids in a controlled manner.

BRIEF DESCRIPTION OF THE DRAWINGS

The following detailed description of the invention will be better understood with reference to the accompanying drawings in which:

FIG. 1 is a front plan view of the device of the present invention;

FIG. 2 is a bottom plan view of the device of the present invention;

FIG. 3 is a section view taken along line 3—3 of FIG. 2;

FIG. 4 is a section view of the device of the present invention showing the assembly of the electrode terminal pins prior to insertion into a molding process;

FIG. 5 is a cross-section taken view along line 5—5 of FIG. 1; and

FIG. 6 is an end view showing the coaxial relationship of the inner electrode and the outer electrode.

DETAILED DESCRIPTION OF THE PREFERRED EMBODIMENTS

Referring to FIGS. 1–5, the surgical device 10 is shown comprising an inner electrode 12 having a first end 14, a second end 16, an outer surface 18, and a channel or cavity 20. The inner electrode 12 is preferably of hollow cylindrical shape whereby fluid may enter the channel 20 through the first end 14 and exit through second end 16. The inner electrode 12 may be designed with different diameters and is preferably made from a high conductive material such as aluminum.

The device 10 further comprises an outer electrode 22 having a first end 24, a second end 26, an inner surface 28, and an outer surface 30. The outer electrode 22 is preferably of hollow cylindrical shape. The outer electrode 22 may also be designed with different diameters so long as such diameters correspond to the associated diameters of inner electrode 12. Outer electrode 22 is also preferably made from a high conductive material such as aluminum.

In the embodiment shown, the inner electrode 12 is positioned inside of the outer electrode 22 in substantially coaxial relationship. The first end 14 of the inner electrode is preferably in substantial alignment with the first end 24 of the outer electrode 22. Further, the first end 14 of the inner electrode 12 is substantially perpendicular to the longitudinal axis of the inner electrode 12. Similarly, the first end 24 of the outer electrode 22 is substantially perpendicular to the longitudinal axis of the outer electrode 22. The second end 16 of the inner electrode 12 preferably extends outward from the second end 26 of the outer electrode 14 a distance b. The distance b is chosen such that jumper wires (to be described) may be electrically connected to the inner electrode 12 and the outer electrode 14.

The device 10 further comprises an insulator 32 disposed between the outer surface 18 of the inner conductor 12 and the inner surface 28 of the outer conductor 22. The insulator 32 is provided to electrically isolate the inner conductor 12 from the outer conductor 14. The insulator 32 may be made from a variety of non-conductive materials. The first end 14 of the inner conductor 12 and the first end 24 of the outer conductor 22 are not provided with any insulation and therefore electrical current may pass from the first end 14 to the first end 24 upon the presence of low resistance tissue or fluid surrounding both the first end 14 and first end 24.

The device further comprises an insulator 34 disposed about the outside surface 30 of the outer electrode 22. The insulator 34 is provided to electrically isolate the outer electrode 22 from the ambient environment. Insulator 34 may also be made from a variety of non-conductive materials. As in the case of insulator 32, the first end 24 of the outer electrode 22 is free of any insulation.

The device 10 further comprises a first terminal pin 36 having a first end 38 and a second end 40. The device 10 further comprises a first jumper wire 42 having a first end 44 and a second end 46. The first end 38 of terminal pin 36 is electrically connected to the first end 44 of the jumper wire 42 by conventional means such as crimping. The second end 46 of the jumper wire 42 is electrically connected to the outer surface 30 of the outer electrode 22 by conventional means such as welding.

The device further comprises a second terminal pin 48 having a first end 50 and a second end 52. The device 10 further comprises a second jumper wire 54 having a first end 56 and a second end 58. The first end 50 of the second terminal pin 48 is electrically connected to the first end 56 of the jumper wire 54 by conventional means such as crimping. The second end 58 of the jumper wire 54 is electrically connected to the outer surface 18 of the inner electrode 12 by conventional means such as welding.

The device 10 further comprises a housing 60 having a front end portion 62, a gripping portion 64, a terminal pin portion 66, and a suction port 68. The gripping portion 64 has side portions 70 and 72 are in generally design to be comfortably and secured grasped by a single hand of the surgeon. The terminal pin portion 66 is provided to securely contain the assembly of the terminal pin 42 and jumper wire 36 and of the terminal pin 48 and the jumper wire 54. The second ends 40 and 52 of the terminal pins 42 and 48, respectively, are exposed to the ambient environment so that may be connected via an electrical cord (not shown) to a bipolar electrosurgical generator (not shown). The suction port 68 comprises an inner channel or cavity portion 74 and an outer portion 76. Outer portion 76 is adapted to engage with suction tubing (not shown) which in turn is connected to a suction device or pump (not shown). The cavity portion 74 of the suction port 68 is in communication with the second end 16 of the inner electrode 12 such that when a control vent (to be described) is partially or fully closed, fluid may flow through the channel 20 of the inner electrode 12 to the suction port 68. The housing 60 further comprises a suction control vent 78 positioned with the center of side portion 70 of the gripping portion 64. The control vent 78 provides communication between the ambient environment and the cavity portion 74 of suction port 68 via a semi-circular channel 80. The dimension of the vent control vent 78 and of the semi-circular channel 80 are chosen such that when the control vent 78 is completely open, there is no fluid flow through the channel 20 of the inner electrode 12 and only air is evacuated from the control vent 78 to the suction port 68.

The device 10 is preferably designed in both a disposable embodiment and a non-disposable embodiment. In the disposable embodiment, the housing 60 is made from a polymer material having a low melting temperature. As such, the device is disposable because sterilization of the device 10 would damage the housing 60. In the non-disposable embodiment, the housing is made from a polymer material having a relatively high melting temperature. As such, the device 10 may be sterilized by conventional processes and reused a number of times without damage to the housing 60. Generally, the higher the melting temperature of the housing 60, the greater the number of times the device 10 can be sterilized after each surgical procedure and re-used.

To manufacture the device 10, the inner electrode 12 is generally first assembled with the outer electrode 22 with insulators 32 and 34 applied thereto. Thereafter, the terminal pins 36 and 48 are electrically connected to the inner and outer electrodes 12 and 22 by jumper wires 42 and 54, respectively. Thereafter, the sub-assembly of the inner and outer electrodes 12 and 22, terminal pins 36 and 48, and jumper wires 42 and 54 are assembled with the housing 60 by an insert injection molding process. The sub-assembly of the inner and outer electrodes 12 and 22, terminal pins 36 and 48, and jumper wires 42 and 54 are placed into a metal mold having the various elements of the housing 60 machined into the mold. Thereafter, the mold is filled under pressure with an appropriate polymer material depending upon whether a disposable or non-disposable device 10 is desired.

To perform an evacuation procedure, a surgeon would activate the suction device or pump and control the fluid evacuation rate by covering all or a portion of the suction control vent. When the suction control vent is open, fluid is caused to evacuate into the first end of the inner electrode, through the channel, and out the suction port to the suction device. To stop the evacuation of fluid, the surgeon removes his/her finger from the suction control vent thereby allowing the same to be exposed to the ambient environment.

To perform a coagulation procedure, a surgeon would turn on the bipolar electrosurgical generator, and depending upon the particular generator used, a surgeon might depress a foot pedal thereby allowing electrical energy to flow to the terminal pins 40 and 52, whereby a localized electrical potential is generated at and between the first end 14 of the inner electrode 12 and the first end 24 of the outer electrode 22.

Alternative Embodiments:

The device 10 has heretofore been described with reference to a preferred embodiment. However, it should be readily apparent that the device 10 may be designed in various other embodiments, made with a variety of different materials, and manufactured by a wide range of processes. By way of example only, the device 10 may be alternatively embodied as follows:

(1) in the embodiment shown, the surface area of the first end 14 of the inner electrode 12 and the surface area first end 24 of the outer electrode 22 are dependant upon the relative inside and outside diameters of the inner electrode 12 and the outer electrode 14. Alternatively, the surface area of the first end 14 or the first end 24 may be increased by re-shaping the first end 14 or the first end 24. By way of example only, the first end 24 of the outer electrode 22 might be chamfered rather than perpendicular to the outer surface 28 of the outer electrode 22.

(2) in the embodiment shown, the terminal pins 42 and 48 are encased within the terminal pin portion 66 and thereby fixed relative to the housing 60. Alternatively, an electrical cord can extend from the terminal pin portion 66 or another portion of the housing 66 and the terminal pins 42 and 48 could be attached to the free end of the electrical cord thereby allowing the terminal pins 42 and 48 to be free of the confines of the housing 60.

(3) in the embodiment shown, the vent control 78 is of substantially uniform rectangular shape. Alternatively, the vent control 78 may take a shape (for example, a rain or tear drop) whereby the width of the vent control changes along its length. Such non-uniform shapes may in some instances make it easier for the operator to control the volume of fluid flow through the channel 20.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

What is claimed is:

1. A bipolar electro-surgical device for use with a suction device and a bipolar electrosurgical generator by a surgeon in an ambient environment to perform coagulation procedures to damaged tissue and evacuation procedures to related fluids, the device comprising:

(a) a first inner electrode having a first end, a second end, an outer surface, and a channel extending from said first end to said second end;

(b) a second outer electrode having a first end, a second end, an inner surface, and an outer surface, said inner surface of said second outer electrode being disposed concentrically about said outer surface of said first inner electrode;

(c) first and second terminal pins each having a first end connected to said first inner and second outer electrodes, respectively, and a second end adapted to engage with the bipolar electrical generator;

(d) an insulator disposed concentrically between said outer surface of said first inner electrode and said inner surface of said second outer electrode in contact with said outer surface of said first inner electrode and said inner surface of said second outer electrode; and (e) a housing comprising:
        a suction port portion, said suction port portion having an inner cavity portion in communication with said second end of said first inner electrode and an outside portion adapted to engage with the suction device,
        a gripping portion, a suction control vent hole disposed in the gripping portion, the vent hole disposed to be coverable by a finger, and
        a channel in the housing extending from the vent hole to the cavity portion to provide fluid communication between the cavity portion of the suction sort portion and the ambient environment;
    wherein the first inner electrode and the second outer electrode protrude from a front portion of the housing, the second end of the second outer electrode terminates at a location between the vent hole and the cavity portion, the first inner electrode extends beyond the second end of the second outer electrode, and the second end of the first inner electrode is located within the cavity portion.

2. The device of claim 1, wherein said first electrode is of substantially cylindrical shape.

3. The device of claim 1, wherein said first electrode is made from aluminum.

4. The device of claim 1, wherein said second electrode is of substantially cylindrical shape.

5. The device of claim 1, wherein said second electrode is made from aluminum.

6. The device of claim 1, further comprising a first jumper wire having a first end connected to said first electrode and a second end connected to said first terminal pin.

7. The device of claim 6 further comprising a second jumper wire having a first end connected to said second electrode and a second end connected to said second terminal pin.

8. The device of claim 7, wherein said first wire is connected to said outside surface of said first electrode and said second wire is connected to said outside surface of said second electrode.

9. The device of claim 1, wherein said housing comprises a one-piece molded housing made from a polymer material having a low melting temperature so that upon sterilization by conventional processes said one-piece molded housing will become damaged.

10. The device of claim 1, wherein the first ends of the first and second terminal pins are connected to the first inner electrode and the second outer electrode at a location between the vent hole and the cavity portion.

\* \* \* \* \*